United States Patent [19]
Martin

[11] Patent Number: 5,408,183
[45] Date of Patent: Apr. 18, 1995

[54] METHOD OF DATING DIFFERENT LEVELS IN A TERRESTRIAL GEOLOGICAL BED USING REMANENT AND INDUCED MAGNETIZATION MEASUREMENTS

[75] Inventor: Jean-Pierre Martin, Colombes, France

[73] Assignee: Compagnie Generale de Geophysique, Massy, France

[21] Appl. No.: 98,058

[22] Filed: Jul. 28, 1993

[30] Foreign Application Priority Data
Jul. 30, 1992 [FR] France ................. 92 09435

[51] Int. Cl.⁶ ........................... G01V 3/26; G01V 3/40
[52] U.S. Cl. ......................................................... 324/346
[58] Field of Search .................. 324/345, 346; 364/422

[56] References Cited
U.S. PATENT DOCUMENTS 3,369,174  2/1968  Groenendyke et al. ............ 324/346
3,965,413  6/1976  Yungul .
4,071,815  1/1978  Zemanek, Jr. ...................... 324/346

FOREIGN PATENT DOCUMENTS
0422985A1  4/1991  European Pat. Off. .

Primary Examiner—Gerard R. Strecker
Attorney, Agent, or Firm—Sughrue, Mion, Zinn, Macpeak & Seas

[57] ABSTRACT

The method of the invention consists in measuring remanent magnetization along a borehole drilled through a geological bed, in detecting the set of reversals in the remanent magnetization, in measuring the induced magnetization at the various levels in said bed, in detecting maxima in the induced magnetization, and in correlating these measurements with known dates, firstly of reversals in the earth's magnetic field and secondly of terrestrial phenomena that have given rise to concentrations of highly magnetic substances, thus making it possible to give dates to the various levels of the bed. The method is particularly applicable to oil prospecting.

6 Claims, 1 Drawing Sheet

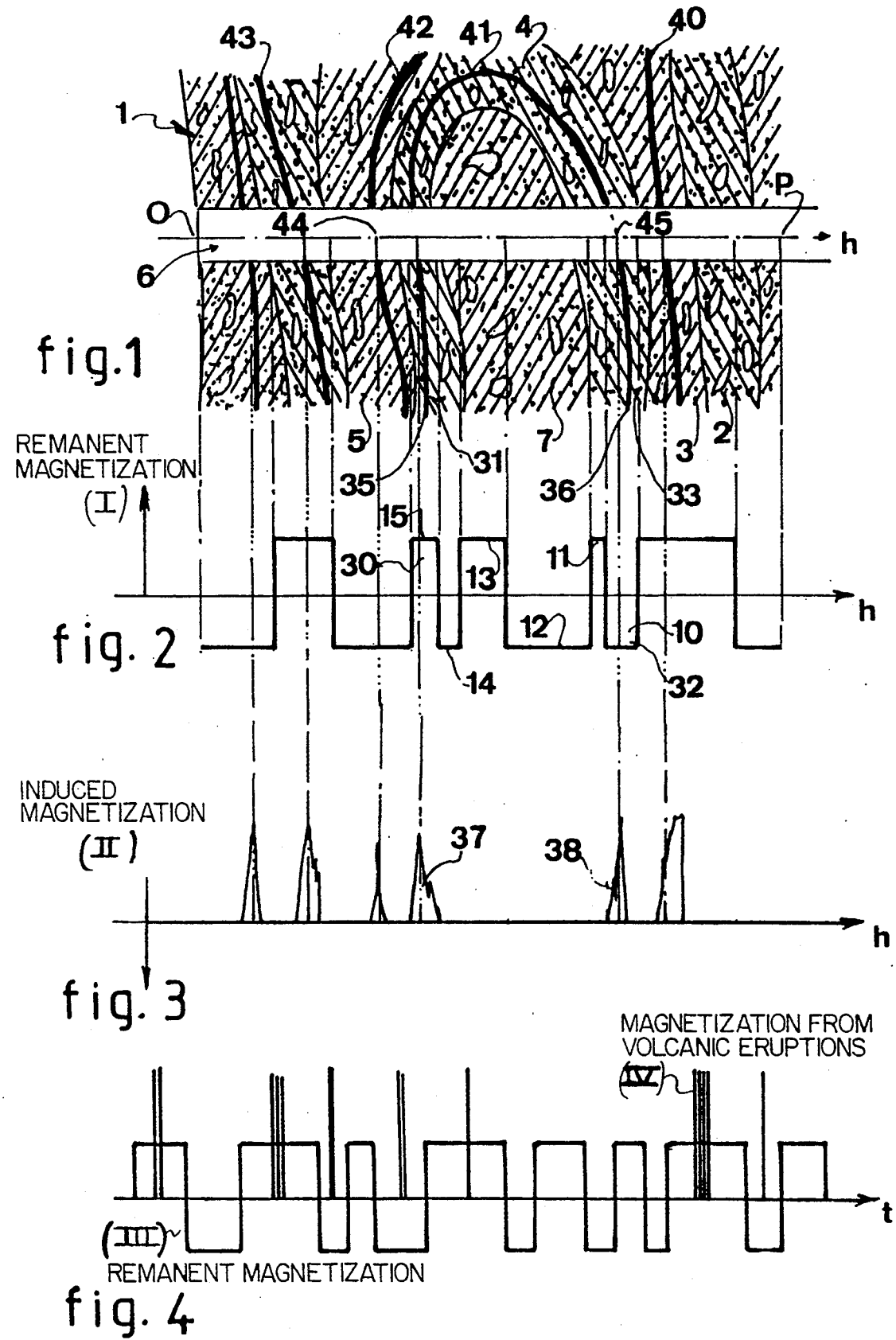

METHOD OF DATING DIFFERENT LEVELS IN A TERRESTRIAL GEOLOGICAL BED USING REMANENT AND INDUCED MAGNETIZATION MEASUREMENTS

The present invention relates to methods of dating various levels in a terrestrial geological bed, and that are of particular application in the field of oil prospecting and exploitation.

BACKGROUND OF THE INVENTION

In order to facilitate searching for oil deposits, determining their quality, and working them optimally, it is highly advantageous to be able to date the various levels of geological beds in which prospecting and working of deposits are undertaken.

Various methods are known for performing such dating, in particular methods that consist in measuring values of remanent magnetization in the various levels of the geological beds being prospected.

Before going any further in the present description, it is necessary to recall that the earth has a magnetic field which is presently directed towards the point called "north", but that over past geological eras, the direction of the magnetic field has switched numerous times between "north" and "south". The magnetization of terrestrial rocks subjected to the earth's magnetic field includes two components: one represents the magnetization induced by the present magnetic field of the earth, referred to by the person skilled in the art as "induced magnetization"; and the other represents "remanent" magnetization corresponding to the magnetization that was induced by the earth's magnetic field as it existed at the time the rocks were formed, such that the rocks retain a record of the field direction at that time.

Thus, to date the various levels of a geological bed, the procedure generally begins by drilling a borehole, advantageously perpendicular to the ground, and then using an apparatus that is known per se, e.g. the apparatus described in French patent FR-A-2 652 911, to measure the remanent magnetization all along the borehole, so as to determine the depths of points at which the direction of the magnetization reverses.

Since it is known when the direction of the earth's magnetic field has reversed in the past, it is theoretically easy to date each level of a bed between two points corresponding to two successive reversals of the earth's magnetic field over a period of time.

The method outlined briefly above gives good results providing the geological beds under investigation were formed uniformly merely by deposition and sedimentation, without the occurrence of phenomena and/or catastrophes such as tilting, faulting, discontinuities due to erosion, etc. Under such circumstances, the strata of geological beds are so thoroughly disturbed that interpreting the results of remanent magnetization measurements along a borehole can lead to uncertainties, gaps, and at worst, to errors in dating.

OBJECTS AND SUMMARY OF THE INVENTION

An object of the invention is thus to implement a method of dating the various levels of a terrestrial geological bed that makes it possible to eliminate a certain number of gaps and/or uncertainties inherent to methods known in the prior art.

More precisely, the present invention provides a method of dating various levels in a terrestrial geological bed, the method comprising:

measuring the remanent magnetization at points situated at different levels in said geological bed;

detecting from the set of said measurements of remanent magnetization, those measurements that correspond to a reversal in the direction of said remanent magnetization and in delivering a first signal representative of the set of reversals of remanent magnetization as a function of said levels;

in measuring the induced magnetization at points situated at different levels in said geological bed;

detecting from the set of said measurements of induced magnetization, those measurements which correspond to maxima in said induced magnetization and in delivering a second signal representative of the set of said maxima in induced magnetization as a function of said levels; and establishing a correlation between said first and second signals and the known dates firstly of reversals of the earth's magnetic field and secondly of terrestrial phenomena that have given rise to concentrations of highly magnetic substances, so as to be able to allocate dates to the various levels of said geological bed.

BRIEF DESCRIPTION OF THE DRAWING

Other characteristics and advantages of the present invention appear from the following description given by way of non-limiting example with reference to the accompanying drawing, in which:

FIG. 1 shows one example of a section through a geological bed for use in explaining how the method of the invention is implemented;

FIG. 2 is a curve showing how a signal representative of remanent magnetization varies at different levels "h" in the geological bed of FIG. 1;

FIG. 3 is a curve showing a signal representative of maxima in the induced magnetization at various levels "h" in the geological bed of FIG. 1; and FIG. 4 is a curve showing how the earth's magnetic field has varied as a function of geological time "t" with, superposed thereon, a curve on the same geological time scale situating terrestrial phenomenon that have given rise to concentrations of substances that are highly magnetic, such as volcanic eruptions.

MORE DETAILED DESCRIPTION

Firstly, it is specified that the various diagrams of FIGS. 1 to 4, whether they relate to the geological bed itself or to the various signals mentioned above are entirely fictional and are given purely by way of illustration for the purpose of explaining the method of the invention.

In order to facilitate searching for oil deposits, determining their quality, and working them optimally, it is highly advantageous to be able to date the various levels of the geological beds in which prospecting and working of deposits are undertaken.

FIG. 1 shows an example of a section through a geological bed 1 having different levels between points "O" and "P", in particular strata 2, 3, 4, 5, 7, . . . that need to be dated in order to deduce the times at which they were formed, and to evaluate the probability of hydrocarbons being present, for example, to see whether it is worth continuing a search for oil.

To date the various levels in the bed 1, the first step is generally to drill a borehole 6, which is advantageously vertical.

Then a device which is known per se is lowered down the borehole for the purpose of measuring variation in the remanent magnetization as measured along the borehole, e.g. between two points "O" and "P".

From these measurements, variations in the remanent magnetization corresponding to reversals in the direction of the remanent magnetization are detected and levels are identified between the two points "O" and "P" of the geological bed at which the remanent magnetization reverses. A first signal is then generated representative of all of the reversals of remanent magnetization as a function of the depth "h" of the levels between the points "O" and "P" of the geological bed 1. Curve I in FIG. 2 shows this first signal which is deduced from measurements of remanent magnetization performed along the borehole 6 between the points "O" and "P".

It should be recalled that the Earth's present magnetic field is directed towards the point called "north", but that over the passage of geological time, the earth's magnetic field has changed direction numerous times between said "north" point and the point called "south". Such reversals are well known in themselves and have been accurately dated in time. It is also known that terrestrial rocks that have been subjected to the earth's magnetic field possess "remanent" magnetization that corresponds to the magnetization induced by the earth's magnetic field as it was at the time the rocks were being formed, so that the rocks constitute a record of the field at that time. One of the two curves shown in FIG. 4, curve III, gives a fictional example of changes in remanent magnetization over geological time "t", in which reversals of said remanent magnetization are easily seen.

If the geological bed between the two points "O" and "P" had been formed uniformly, i.e. if the various strata defined between said two points had been deposited one on another without being subjected to any significant disturbances over the course of geological time, then by correlating curves I and III, it would be possible to date those levels within the geological bed 1 being prospected at which reversals occurred in the earth's magnetic field.

However, for strata that have been subjected to disturbances and/or catastrophes, such as folding, tilting, etc., their final appearance may be as shown by way of illustration in FIG. 1. In geological bed 1, the stratum identified by reference 4 has folded and imprisoned stratum 7, and the signal delivered by the measurement device therefore detects a remanent magnetization direction 30 for the upper portion 31 of stratum 4 and an opposite direction 32 for the lower portion 33 of the same stratum 4. Curve I representing the first signal therefore shows up a number of reversals in remanent magnetization, e.g. reversals 10, 11, 12, 13, 14, and 15 that is greater than the number of reversals that took place in reality. Consequently, the first signal is erroneous and it can become impossible to establish a correlation between the two curves I and III, and thus impossible to date all of the various levels between the points "O" and "P".

In this case, there exists uncertainty or a gap in the dating of the various levels of geological bed 1.

In many cases, the method of the invention makes it possible to remove such uncertainty or gaps.

It is known that in the course of geological time, terrestrial phenomena have occurred giving rise to significant concentrations of highly magnetic substances, in particular magnetite. Such phenomena include major volcanic eruptions that produced effects over vast areas of the Earth, and large changes in glaciers such as glaciers advancing or retreating, that have concentrated highly magnetic materials, in particular, over large areas. The large majority of such phenomena have been identified and listed, particularly with respect to their duration, quantity, and the nature of the substances ejected or collected. Curve IV in FIG. 4 is plotted to the same geological time scale "t" as curve III and provides a fictional example making it possible to situate known volcanic eruptions of different sizes in time.

It is also known that the substances emitted during volcanic eruptions include substances that are highly magnetic, e.g. the substance known as "magnetite", one of whose properties is to cause the induced magnetization in such substances to be much stronger than the induced magnetization in ordinary rocks contained in geological beds. Strata that were deposited following the fallout of substances ejected during volcanic eruptions therefore have considerably stronger induced magnetization than strata that do not contain such substances.

Thus, to implement the method of the invention, e.g. using the same device as mentioned in the preamble of the present description, measurements are extracted from the induced magnetization measured along a borehole 6, e.g. by filtering, said measurements corresponding solely to "maximum" values of the induced magnetization, i.e. values that exceed a predetermined threshold. This set of filtered portions of the measurements constitutes a second signal generally made up of peaks, as shown by curve II in FIG. 3 which is a function of the depth "h" of the various levels in the geological bed 1. This second signal therefore makes it possible to identify those levels in the geological bed 1 that correspond to induced magnetization which is much stronger than adjacent higher or lower levels, i.e. to identify levels in the geological bed that correspond to deposits including highly magnetic substances due to the fallout from volcanic eruptions, with each peak in FIG. 1 corresponding substantially to a thick continuous line 40, 41, 42, Or 43 that represents such a deposit.

By correlating curve II representing the second signal and curve IV representing the set of known volcanic eruptions as a function of time, it is possible to solve some uncertainties or to fill in certain gaps in the dating of the various levels in a geological bed.

For example, with reference to the geological bed 1 shown in FIG. 1, dating is initially performed using the previously known method, i.e. by correlating curve I with curve III. Correlating curve II with curve IV, serves to date certain levels in layer 1 with certainty since volcanic eruptions are generally easily distinguished from one another, unlike reversals of remanent magnetization.

In the example shown, it can also be seen that if one of the two portions 37 and 38 of the second signal of curve II (e.g. portion 38) corresponds to a known volcanic eruption, then the other portion 37 corresponds a priori to no known eruption. However, since these portions are symmetrical to each other in an axial direction, it is highly probable that these two portions 37 and 38 of curve II are representative of the induced magnetization in a single deposit of volcanic fallout. It is thus possible to deduce that the portions of strata 31 and 33 which respectively contain portions 35 and 36 of deposited volcanic fallout belong to the same stratum that has been folded, like the stratum 4 in the example shown.

The uncertainty that would otherwise exist in dating levels between the two points 44 and 45 in bed 1 which belong to respective portions of strata 31 and 33 can thus be removed by the method described above.

The example given above with reference to volcanic eruptions can be applied in the same way to the effects of glaciers, which are similarly catalogued, for the most part.

I claim:

1. A method of dating various levels in a terrestrial geological bed, even when the bed is formed non-uniformly, the method comprising:

measuring the remanent magnetization at points situated at different levels in said geological bed;

detecting from the set of said measurements of remanent magnetization, those measurements that correspond to a reversal in the direction of said remanent magnetization and in delivering a first signal representative of the set of reversals of remanent magnetization as a function of said levels;

measuring the induced magnetization at points situated at different levels in said geological bed;

detecting from the set of said measurements of induced magnetization, those measurements which correspond to maxima in said induced magnetization and in delivering a second signal representative of the set of said maxima in induced magnetization as a function of said levels; and comparing said first and second signals and the known dates firstly of reversals of the earth's magnetic field and secondly of terrestrial phenomena that have given rise to concentrations of highly magnetic substances, in order to identify redundant ones of said first and second signals caused by the folds or bends of a non-uniform bed, so as to be able to more accurately allocate dates to the various levels of said geological bed.

2. A method according to claim 1, wherein the terrestrial phenomena that has given rise to concentrations of highly magnetic substances are volcanic eruptions.

3. A method according to claim 1, wherein the terrestrial phenomenon that has given rise to concentrations of highly magnetic substances are movements of glaciers.

4. A method of dating various levels in a terrestrial geological bed, even when the bed is formed non-uniformly, the method comprising:

measuring the remanent magnetization at points situated at different levels in said geological bed;

detecting from the set of said measurements of remanent magnetization, those measurements that correspond to a reversal in the direction of said remanent magnetization and in delivering a first signal representative of the set of reversals of remanent magnetization as a function of said levels;

measuring the induced magnetization at points situated at different levels in said geological bed;

detecting from the set of said measurements of induced magnetization, those measurements which correspond to maxima in said induced magnetization and in delivering a second signal representative of the set of said maxima in induced magnetization as a function of said levels;

comparing said first signals with the known dates of reversals of the earth's magnetic field;

comparing said second signals with the known dates of terrestrial phenomena that have given rise to concentrations of highly magnetic substances; and allocating dates to the various levels of said bed based on the results of said comparing steps.

5. A method according to claim 4, wherein the terrestrial phenomenon that has given rise to concentrations of highly magnetic substances are volcanic eruptions.

6. A method according to claim 4, wherein the terrestrial phenomenon that has give rise to concentrations of highly magnetic substances are movements of glaciers.

* * * * *